(12) United States Patent
Riha-Scott et al.

(10) Patent No.: US 10,888,470 B2
(45) Date of Patent: Jan. 12, 2021

(54) ABSORBENT REUSABLE CLOTHING AND UNDERGARMENTS

(71) Applicant: RSD Holdings Limited, Auckland (NZ)

(72) Inventors: Frantisek Riha-Scott, Auckland (NZ); Mark Nairn Davey, Auckland (NZ)

(73) Assignee: RSD HOLDINGS LIMITED, Auckland (NZ)

( * ) Notice: Subject to any disclaimer, the term of this patent is extended or adjusted under 35 U.S.C. 154(b) by 661 days.

(21) Appl. No.: 14/660,318

(22) Filed: Mar. 17, 2015

(65) Prior Publication Data
US 2015/0290049 A1    Oct. 15, 2015

(30) Foreign Application Priority Data

Apr. 11, 2014  (NZ) .................................... 623773

(51) Int. Cl.
*A61F 13/49*    (2006.01)
*A61F 13/505*   (2006.01)
*A41B 9/00*     (2006.01)

(52) U.S. Cl.
CPC .......... *A61F 13/505* (2013.01); *A41B 9/001* (2013.01); *A41B 9/004* (2013.01); *A61F 13/49006* (2013.01); *A41B 2400/52* (2013.01)

(58) Field of Classification Search
CPC ............ A61F 13/15268; A61F 13/505; A61F 13/51496; A61F 13/49006; A61F 2013/15276; A61F 2013/8497
USPC ................................................ 604/385.15
See application file for complete search history.

(56) References Cited

U.S. PATENT DOCUMENTS

| 2,255,931 | A | * | 9/1941 | Kloster | ............... | A41B 9/02 2/404 |
| 2,664,889 | A | * | 1/1954 | Bailey | ............... | A41B 9/02 2/403 |
| 3,517,666 | A | * | 6/1970 | Atlee | ............... | A41B 9/02 2/403 |

(Continued)

FOREIGN PATENT DOCUMENTS

| BE | 1010279 | 5/1998 |
| DE | 44 29 251 | 2/1996 |

(Continued)

OTHER PUBLICATIONS

Office Action dated Apr. 5, 2017 in U.S. Appl. No. 13/876,105.*

(Continued)

*Primary Examiner* — Catharine L Anderson
(74) *Attorney, Agent, or Firm* — Nixon & Vanderhye

(57) ABSTRACT

Absorbent, launderable garments and undergarments for incontinent or other persons likely to discharge fluids from time to time are supplied in many styles and capacities. All include a shaped absorbent pouch assembly, having an inner conformable and permeable layer in contact with the skin and an absorbent cotton layer sealed under a gas-permeable yet waterproof and stretchable textile. The pouch is positioned by a set of elastic strips or sheet elastic fabric; each set being visually similar to a style of regular underwear. A preferred waterproofing treatment uses an emulsion of fluoroalkyl acrylate permeated into a knitted or woven textile. In higher capacity versions the entire garment is waterproofed.

8 Claims, 6 Drawing Sheets

(56) References Cited

U.S. PATENT DOCUMENTS

| | | | | | |
|---|---|---|---|---|---|
| 4,302,485 | A | * | 11/1981 | Last | D06M 10/02 118/419 |
| 4,326,302 | A | * | 4/1982 | Lowe | A61F 5/4401 2/405 |
| 4,338,938 | A | * | 7/1982 | Seavitt | A61F 13/49004 604/377 |
| 4,365,049 | A | * | 12/1982 | Tsunoda | C08F 220/24 430/197 |
| 4,397,646 | A | * | 8/1983 | Daniels | A61F 13/49004 604/381 |
| 4,516,975 | A | * | 5/1985 | Mitchell | A61F 13/49004 604/385.15 |
| 4,555,245 | A | * | 11/1985 | Armbruster | A61F 5/4401 2/403 |
| 4,690,681 | A | * | 9/1987 | Haunschild | A61F 13/496 604/396 |
| 4,880,424 | A | * | 11/1989 | Rautenberg | A61F 13/66 2/401 |
| 4,961,736 | A | * | 10/1990 | McCloud | A61F 13/49004 604/385.15 |
| 5,029,345 | A | * | 7/1991 | Angheluta | A41B 9/023 2/403 |
| 5,087,253 | A | * | 2/1992 | Cooper | A61F 5/4401 604/385.15 |
| 5,098,419 | A | * | 3/1992 | Gold | A41B 9/004 2/401 |
| D325,256 | S | * | 4/1992 | Landsman | D24/124 |
| 5,122,407 | A | * | 6/1992 | Yeo | A61F 13/512 428/138 |
| 5,157,793 | A | * | 10/1992 | Michels | A41B 9/02 2/401 |
| 5,185,011 | A | * | 2/1993 | Strasser | A61F 13/49004 604/385.15 |
| 5,209,743 | A | * | 5/1993 | Hardison | A61F 13/49004 2/111 |
| 5,210,882 | A | * | 5/1993 | Moretz | A41B 9/004 2/400 |
| 5,300,054 | A | | 4/1994 | Feist et al. | |
| 5,344,698 | A | * | 9/1994 | Rock | A41D 31/02 428/913 |
| 5,454,799 | A | * | 10/1995 | Lakiss-Smith | A61F 13/49004 604/358 |
| 5,546,607 | A | * | 8/1996 | Roberts | A61F 13/49 2/400 |
| 5,562,648 | A | * | 10/1996 | Peterson | A61F 13/512 604/370 |
| 5,733,275 | A | * | 3/1998 | Davis | A61F 13/5605 604/387 |
| 5,964,743 | A | * | 10/1999 | Abuto | A61F 13/5323 604/368 |
| 6,061,839 | A | * | 5/2000 | Smolik | A61F 13/471 2/400 |
| 6,195,800 | B1 | * | 3/2001 | Gilmer | A41B 13/04 2/238 |
| 6,362,389 | B1 | * | 3/2002 | McDowall | A61F 13/531 604/364 |
| 6,423,047 | B1 | * | 7/2002 | Webster | A61F 13/505 604/378 |
| 6,559,208 | B2 | * | 5/2003 | Ho | C08F 255/02 428/500 |
| 6,660,339 | B1 | * | 12/2003 | Datta | C23C 14/12 427/255.5 |
| 6,746,491 | B2 | | 6/2004 | Lack | |
| 6,782,557 | B1 | * | 8/2004 | Feder | A61F 13/15268 2/400 |
| 6,848,121 | B1 | * | 2/2005 | Halid | A61F 13/66 2/400 |
| 7,678,094 | B1 | * | 3/2010 | Cannon | A61F 13/49006 604/378 |
| 8,460,265 | B1 | * | 6/2013 | Calender | A61F 13/49006 2/401 |
| 2002/0102892 | A1 | * | 8/2002 | Lack | D06M 13/432 442/85 |
| 2003/0114547 | A1 | * | 6/2003 | Hara | D06M 13/144 521/50 |
| 2003/0120243 | A1 | * | 6/2003 | Uitenbroek | A61F 13/4902 604/385.16 |
| 2004/0202818 | A1 | * | 10/2004 | Yamamoto | D06M 11/05 428/96 |
| 2004/0230175 | A1 | * | 11/2004 | Rainville-Lonn | A61F 13/74 604/396 |
| 2005/0215145 | A1 | * | 9/2005 | Guerrero | A41D 31/02 442/59 |
| 2006/0189955 | A1 | * | 8/2006 | Miskie | A47C 27/005 604/385.15 |
| 2006/0206077 | A1 | * | 9/2006 | Warren | A61F 13/5514 604/385.02 |
| 2007/0142812 | A1 | * | 6/2007 | Popp | A61F 13/51464 604/385.22 |
| 2008/0108967 | A1 | * | 5/2008 | Mizushima | A61F 13/496 604/385.23 |
| 2008/0178368 | A1 | * | 7/2008 | Clark | A41B 9/02 2/403 |
| 2008/0222781 | A1 | * | 9/2008 | Rhew | A41B 9/004 2/406 |
| 2009/0181588 | A1 | * | 7/2009 | Capwell | D06M 11/44 442/64 |
| 2010/0179502 | A1 | * | 7/2010 | Roe | A61F 13/49003 604/385.15 |
| 2011/0094017 | A1 | | 4/2011 | Strange et al. | |
| 2012/0010582 | A1 | * | 1/2012 | Newnam | A61F 13/505 604/360 |
| 2012/0029462 | A1 | * | 2/2012 | Dobrin | A61F 13/62 604/389 |
| 2012/0164906 | A1 | * | 6/2012 | Yahiaoui | B32B 5/12 442/376 |
| 2012/0220976 | A1 | * | 8/2012 | Morse | A61F 13/496 604/385.15 |
| 2012/0282425 | A1 | * | 11/2012 | Gallagher | A41D 27/245 428/61 |
| 2014/0013490 | A1 | * | 1/2014 | Evenson | A61F 13/49004 2/400 |
| 2014/0025027 | A1 | * | 1/2014 | Png | A61F 13/49006 604/371 |
| 2014/0039432 | A1 | * | 2/2014 | Dunbar | A61F 13/49003 604/360 |
| 2014/0378936 | A1 | * | 12/2014 | Coates | A61F 13/505 604/396 |
| 2015/0074874 | A1 | * | 3/2015 | Ferber | A41D 1/06 2/401 |
| 2016/0184146 | A1 | * | 6/2016 | Tulk | A61L 15/46 514/560 |
| 2016/0296384 | A1 | | 10/2016 | Png et al. | |

FOREIGN PATENT DOCUMENTS

| | | |
|---|---|---|
| JP | 2014-29052 | 2/2014 |
| WO | 2014/007343 | 1/2014 |
| WO | 2014-026236 | 2/2014 |

OTHER PUBLICATIONS

Office Action dated Dec. 22, 2017 in U.S. Appl. No. 13/876,105.*

Fado et al., Absorbent products for urinary/faecal incontinence: a comparative evaluation of key products designs Health Technology Assessment (2008) 12 No. 29.

Beguin et al., "Improving diaper design to address incontinence associated dermatitis" BMC Geriatrics (2010) 10:86.

Baker et al., "Evaluation of absorbent products for women with mild to moderate urinary incontinence" Applied Nursing Research 9; No. 1 (Feb. 1996) 29-36.

* cited by examiner

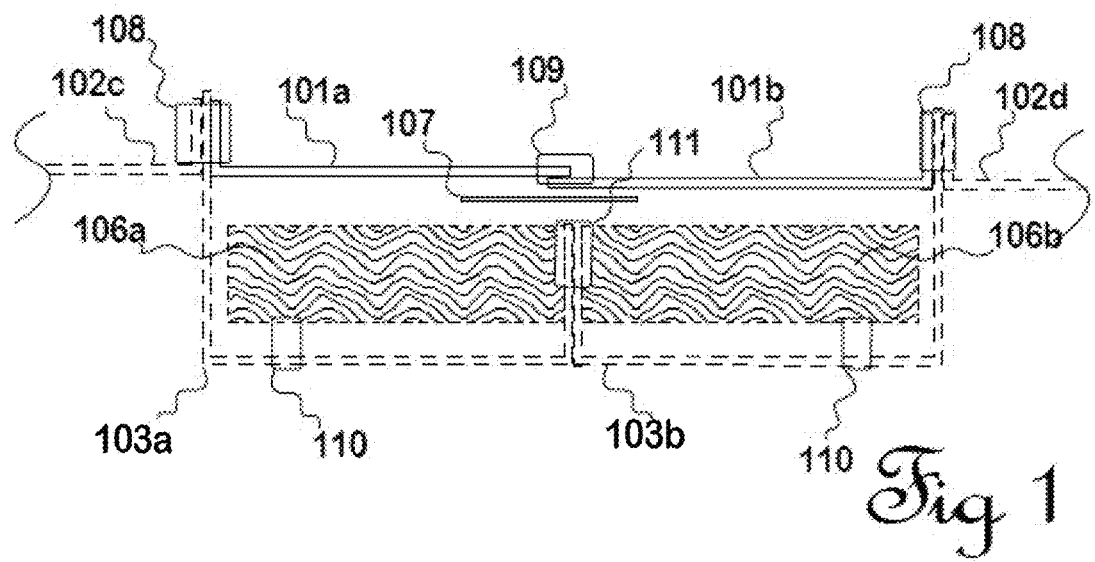
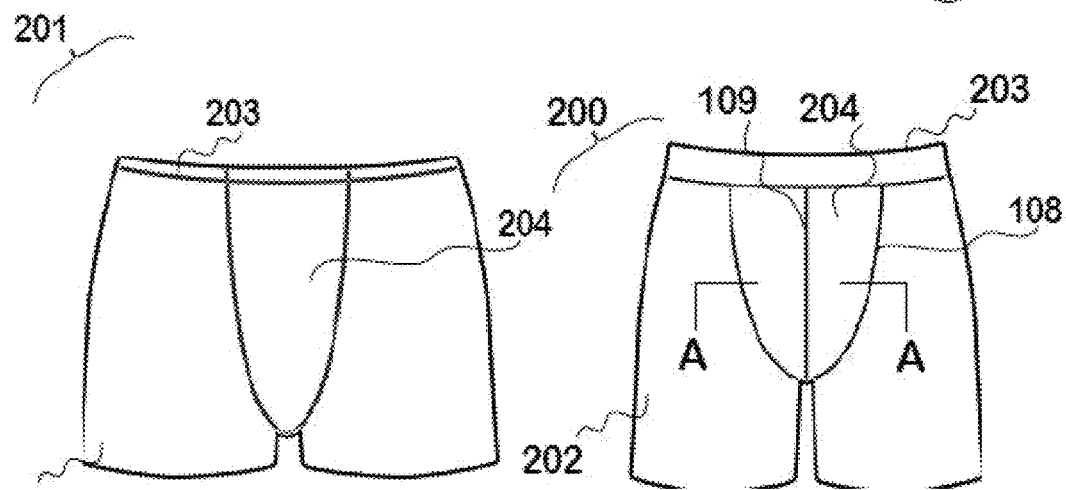
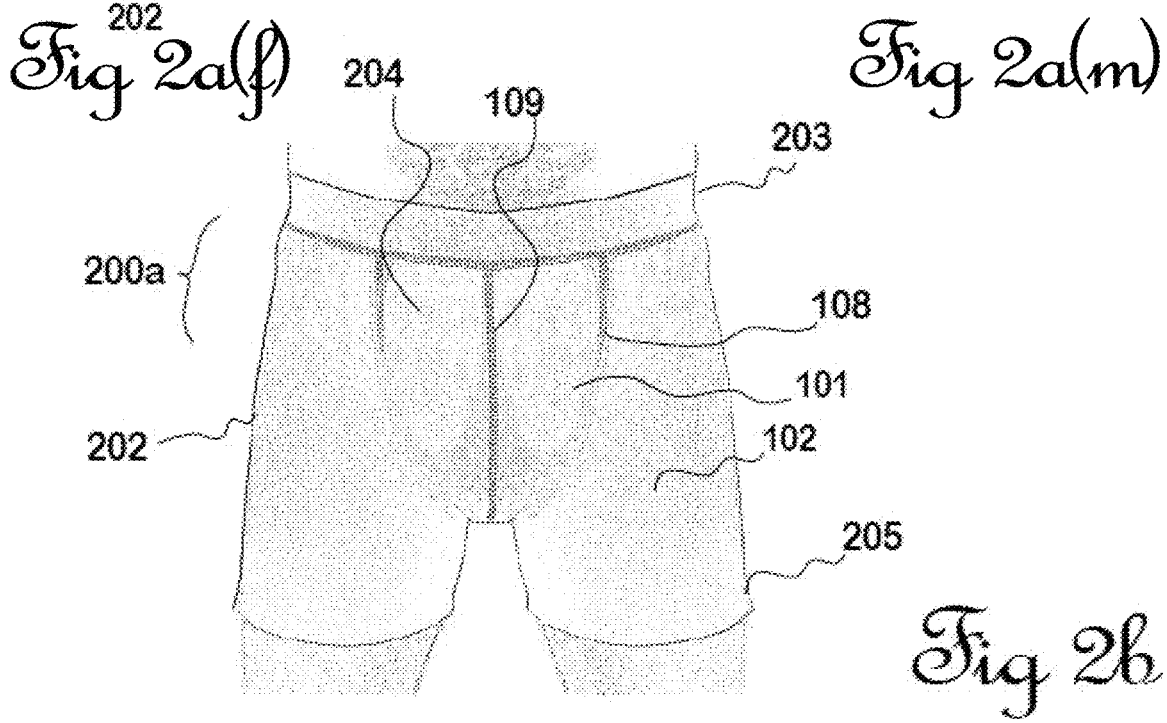

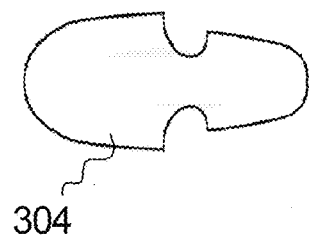
304
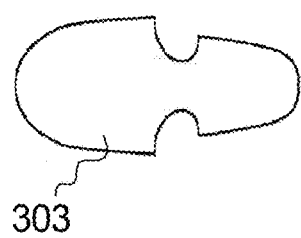
303
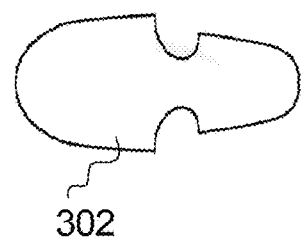
302
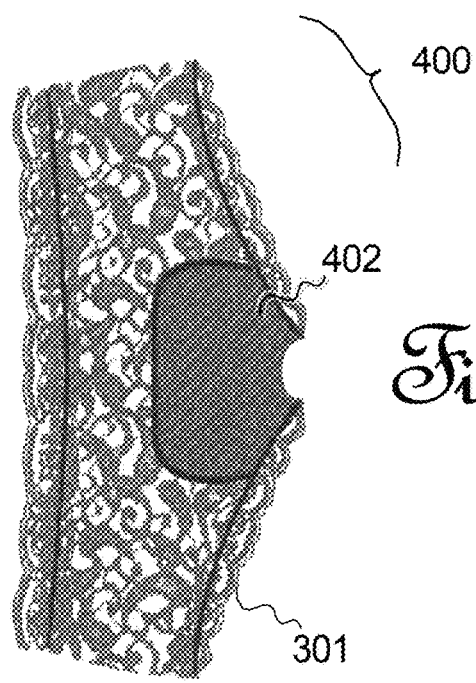
Fig 4
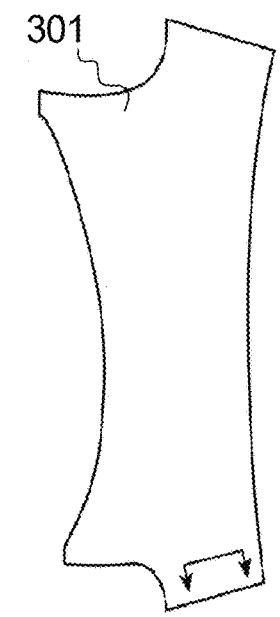
Fig 3
Fig 5a
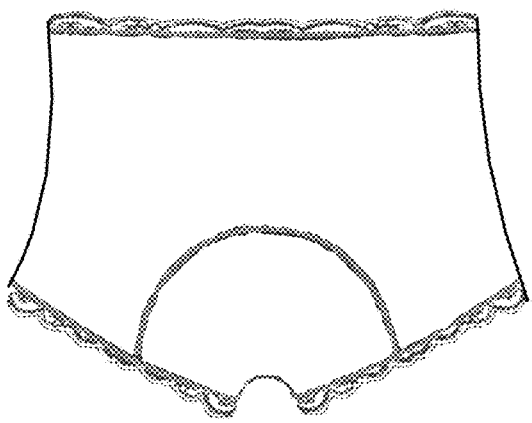
Fig 5b

ABSORBENT REUSABLE CLOTHING AND UNDERGARMENTS

FIELD

This invention relates to absorbent, washable and re-usable undergarments with a capability for absorbing and retaining discharged material inside a waterproofed space; more particularly to unobtrusive underpants or panties for incontinent persons or the like.

Definitions

This document uses the word "textile" to refer to a woven or knitted textile or fabric. Any non-woven panel or portion that is included in the invention is specifically identified.

In this document, "Inner" refers to a place or layer worn against the person's body.

"Pad" refers to a washable and re-usable absorbent material comprised of one or more layers, such as a woven material known as "cotton tufting", "cotton towelling", or "microfiber cotton". and should not be taken as a disposable-type pad for catamenial discharges.

"Conform" is used to describe a property of a sheet of a cloth or fabric to be able to lie closely over a convex shape as a result of being flexible and elastic, and, unlike a sheet of plastic, being able to stretch or shrink.

"Discharge" most likely comprises one or more of: urine, feces, diarrhoea, intestinal contents, mucus, catamenial discharge, post-partum discharge, and drainage from an infection. Garments exist for catching such discharges; the best-known example being nappies or diapers for babies and others. Discharge may occur continuously, or intermittently at a slow or fast flow rate. The discharged material is almost without exception offensive, malodorous, and presents a health hazard if inadvertently released in public areas, or is disposed of in disposable undergarments.

Reference is often made herein to a "quick dry" layer, such as the inner layer of the absorbent pouch assembly that is a consistent part of this garment. The preferred layer is known as "a functional 100% polyester fabric" or textile. It is easily wetted and is highly water-permeable. It is often referred to as "dri-cool" or "dry-cool" and is supplied by a large number of manufacturers. It may include fibers of elastane (Spandex®) for stretchability.

BACKGROUND

An estimate for the proportion of a population affected by incontinence is one in six persons; likely to rise with the growing number of elderly persons in the community. The Applicant's trials included persons who would inadvertently release urine 20 times during one test. Beguin et al state that over 42% of women over 60 experience a moderate to severe urinary incontinence. Baker et al state that the US absorbent pad market was US$496 million in 1987, with up to 40% of adult women affected. Irwin et al summarised the position for the worldwide population in 2008 as: 10.7% were affected by overactive bladder and 8.2% were affected by urinary incontinence. They found the majority of affected persons were in Asia. A July 2013 report by Companies and Markets.com expected the incontinence market in the USA to reach US$1.6 Bn in 2017. Such reports indicate that there is a substantial problem and a significant market demand, or long-felt want.

In some cases incontinence is temporary; in others it is a consequence of advancing age or disease. Incontinence has been described as one of 5 types: overflow, stress (ie pressure), urge, functional and reflex. The condition can be embarrassing to the afflicted person especially since present "prosthetic" garments are obvious to others and carry a stigma and stereotype denigrating the person of any age—not just older people—using them. For instance, one survey noted that the fastest growing US market is to obese African-American women aged between 20 and 30. Clothing that effectively conceals incontinence, by both (a) effectively containing any leakage including odors, and (b) by not looking at all like incontinent garments would be desirable. Conditions such as urinary retention in the elderly female population may be exacerbated by a fear of inadvertent release. Effective garment security is needed.

Beyond incontinence as an actual disease or syndrome, some occupations such as police or soldiers on extended duty including crowd control, and airplane pilots, need to wear clothing capable of absorbing urine from a bladder that has filled over time. In addition, marathon runners, other sports persons, and travellers may need such clothing.

The cost of dealing with an incontinence or similar problem is raised if the garments provided cannot be laundered and used again.

One requirement of absorbent underwear is that it should allow a person to carry on wearing the same outer clothing that they used to wear before onset of incontinence. The absorbent clothing should not give out any clues that it is present, and has an absorbent function. Prior-art clothing is characteristically bulky, clearly utilitarian, lacking any sense of aesthetics, and is not designed for comfort. Some types make a rustling noise as the person moves, arising from plastic membranes around absorbent pads. A "wet feeling" is uncomfortable and is another disadvantage to be overcome. Transfer of any discharge to outer garments is highly undesirable. People with wet skin areas, especially between the legs or in skin folds are likely to suffer from incontinence-associated dermatitis or vaginal infections. It is desirable to maintain the person's skin dry and aerated.

Also desirable is a "low-maintenance" attribute so that underwear can be laundered and dried as a single unit without having to be, for example, disassembled while dirty, partly discarded, and reassembled.

Many, usually disposable garments that claim a waterproof property intended to keep discharges within the garment include a thin membrane typically of polyurethane or sometimes of polyethylene as the water barrier. Disadvantages of this include: poor breathability (regarding gases), short life, perceptible rustling noise. We suspect that a membrane of perhaps 0.25 mm thickness will not last for many washes especially if detergents with strong disinfectants are used, although there is a variety of types of "polyurethane". Clothing capable of successfully managing the flow of moisture and liquids across a textile barrier is known, such as "Goretex®" raincoats that keep the rain out yet pass perspiration outward, so that the user does not become soaked, uncomfortable, or overheated.

A further need that arises in some circumstances is the ability of the garment to contain urine released at a micturition rate, even if it is not absorbed at the same rate. This requirement can be met with the invention to be described. Prior-art garments seem best at containing slow discharges, although Feist et al U.S. Pat. No. 5,300,054 and Bergman et al EP 0343941 addressed the problem for disposable diapers. Fado et al report that the incontinent washable garments style that were surveyed had failed to contain high-rate discharges.

PRIOR ART

Re-usable or disposable diapers that include pads and panty liners for babies and for children or incontinent adults are well known. They are intended to have a high capacity for absorbing liquids and semisolids. Many are disposable, and non-woven. Many are made from synthetic materials that raise a risk of an inflammatory effect on the skin especially in older persons. Many prior-art diapers stop absorbing after a while if left on the patient. Water vapor permeability is a desirable attribute but is not always provided, so the skin may remain wet.

A selection from the prior art includes Feist et al U.S. Pat. No. 5,300,054 describing a disposable diaper adequate for adult use. An absorbent gelling material is used, and a polyethylene water barrier is used on the exterior. An exterior waterproofing film comprised of two layers of polyurethane having two differing average pore sizes is claimed to prevent loss of performance after repeated laundering. Much of the prior art describes layered discharge holding means with a waterproof exterior, an absorbent mass, and a hydrophilic interior side. DE4429251 describes a re-usable garment for incontinent persons, including a pocket for male genitalia. It also includes a pocket for a disposable absorbent pad, hence is not an equivalent of the present invention. Similarly, WO2014/026236 describes a launderable gusset or insert having an inner layer treated to become hydrophilic, an intermediate absorbent layer, and an outer breathable but substantially moisture-resistant layer, for insertion into clothing. Then, that outer layer is concealed behind a layer of clothing which would tend to reduce the efficiency of the outer, breathable layer. The gusset does not appear to be able to conform to the shape of the person's body.

BE1010279 also describes a re-usable garment for incontinent persons. The overall construction provides a median open channel that exposed the absorbent material of the garment to the person wearing the garment. The restricted space would inherently limit the peak absorbtion rate, and waterproofing relies on a polyurethane film. Comfort cannot be assessed. U.S. Pat. No. 6,746,491 describes treatment of garments with a specialised mixture including fluoroalkyl acrylate among other active materials, to make a wrinkle-free waterproofed garment presumably for military uniforms; but does not mention undergarments. US2011/0094017 describes a waterproof panty with rolled-over seams.

In summary, none of the prior art discloses a repeatedly launderable and reusable garment or undergarment for absorbing inadvertent body discharges that has a visible and apparently normal waterproofed external surface located over the absorbent pouch.

REVIEW-TYPE LITERATURE

Fado et al "Absorbent products for urinary/fecal incontinence: a comparative evaluation of key product designs" *Health Technology Assessment* (2008) 12 no. 29

Beguin et al "Improving diaper design to address incontinence associated dermatitis" *BMC Geriatrics* (2010) 10:86

Baker J et al "Evaluation of absorbent products for women with mild to moderate urinary incontinence" *Applied Nursing Research* 9; No. 1 (February 1996) 29-36

Irwin D E et al, "Worldwide prevalence estimates of lower urinary tract symptoms, overactive bladder, urinary incontinence and bladder outlet obstruction" BJUI 108; 1132-1139 (2011)

Problem to be Solved

There is a need for re-usable clothing and more particularly underwear that has a capacity to absorb, at any likely rate of discharge, liquids or semi-solids discharged from a person's body, does not leak the absorbed materials beyond the outer surface of the protector, and does not emit odours, while being comfortable, pervious to water vapour, and aesthetically acceptable to the person and to others. Underwear that conveys the liquid away from the skin by means of capillary flow is desirable. Further, the absorbency property is preferably maintained over time to take advantage of evaporation from the pad through a gas-permeable waterproof exterior. In hot climates this undergarment may comprise the only garment worn. Any person having less than perfect control over release of fluids from their body, such as incontinence arising from bladder or bowel or catamenial fluids or post-partum fluids would appreciate spill-capable, reassuring yet unobtrusive absorbent clothing. People who have incontinence are embarrassed about it. The cited literature describes the generally inadequate incontinence products of the times.

Object

An object of the present application is to provide improved and re-usable clothing capable of absorbing moisture and liquid discharges such as incontinent discharges from bladder, bowel or catamenial fluids emanating from the body of a wearer, or at least to provide the public with a useful choice.

SUMMARY OF INVENTION

In a first broad aspect the invention provides a washable and reusable undergarment for a person, adapted for absorbing and retaining one or more discharges released from an at-risk area of a person's body through one or more orifices, wherein the garment includes an absorbent pouch assembly having an interior, an inner aspect, an external aspect and sides; the inner aspect of the pouch being, when in use, positioned close to or in contact with the at-risk area by pouch retaining means that are attached to the pouch and that are supported by the person's body; the retaining means being selected from a range including elastic cords, elastic waist bands, and elastic fabric panels including trunk/leg panels; the retaining means resembling regular garments or undergarments; the inner aspect comprising at least one shaped panel comprised of a skin-conformable, wettable and permeable textile, the inner aspect surrounding and in contact with a base and sides of a flexible and shaped absorbent pad having an inner face, an outer face and at least one side and comprised of an amount of a wettable and fluid-absorbent composition, the interior of the absorbent pouch assembly being sealed at the external aspect by at least one outer shaped panel of a textile having a conformable, hydrophobic and gas-permeable composition.

Preferably, the inner aspect of the absorbent pouch comprises a knitted or woven elastic and hydrophilic textile and the skin-conformable property of the inner aspect is provided by inclusion in the textile of elastic fibers selected from a range including elastane; the preferred textile being known as "quick dry" functional 100% polyester.

Preferably, the absorbent pad inside the absorbent pouch is comprised of at least one layer of an amount of absorbent fibrous material selected from a range including tufted towelling and cotton and is flexible.

In a related aspect, an inner portion of the pad is constructed to be relatively open and permeable to flow as compared to a relatively dense outer portion of the pad, thereby facilitating reception of incoming liquid material at a flow rate characteristic of micturition.

In a further related aspect, the garment or more particularly the pad includes active ingredients selected from a range including colloidal silver and activated carbon; optionally in a layer.

In a further aspect, the garment or undergarment is provided in a "G-string" style wherein the absorbent pouch assembly is held in place by a waist cord from each anterior side and a posteriorly directed cord or thong, wherein textile panels beyond the pouch are absent.

In a second broad aspect, the outer shaped panel of the pouch is an elastic knitted or woven textile and has been subjected to a waterproofing process.

Preferably the waterproofing process comprises a water-repellent material selected from a range including fluoroalkyl acrylate that has been permeated into the textile used for the outer shaped panel thereby forming a waterproof, hydrophobic yet gas-permeable panel; the textile retaining previous elastic properties.

In a related aspect at least one seam passing between the interior of the absorbent pouch assembly and an external environment is rendered waterproof by use of a water-impervious material being selected from the range of: a silicone-impregnated tape, a tape impregnated with the plastics polytetrafluorethane (PTFE), including a heat-sealable tape; a silicone-rich paint, or a water-repellent silicone ink in order that liquids cannot be transferred by wicking through the seam from inside the absorbent pouch assembly to the exterior; at least for some Styles.

Preferably elastic bands around leg openings are provided; at least for the Styles intended for higher capacities.

Preferably the trunk/leg panels are shaped and are comprised of woven or knitted or lace and the panels are a stretchable textile.

In a related aspect, the trunk/leg panels are constructed from a waterproofed fabric, waterproofed according to this invention.

Preferably, the garment or undergarment is produced in a range of nominal capacities for holding released fluid of between 30 ml and 500 ml.

Preferably, the garment or undergarment is produced in a range of body sizes of between XS (for children) and 6XL (for large adults).

Preferably, the garment or undergarment is produced using a textile selected from a range of textiles (including lace) having colors, configurations and styles such that any one garment or undergarment is similar in outward appearance and style to regular underpants, briefs, panties, G-strings, or other undergarments in order that the person wearing the garment does not perceive discrimination, embarrassment, or discomfort.

In a further aspect, the garment or undergarment includes men's styles adapted for wearing by the provision of an internal space capable of accommodating the male genitalia.

Preferably, the garment includes men's styles adapted by inclusion of a fly aperture at one side of the internal space.

Preferably, for the high-capacity versions, the trunk/leg panels are comprised of an outer stretchable layer of a waterproofed, gas-permeable textile and an inner stretchable layer comprised of a wettable, liquid-absorbent, gas-permeable textile layer.

Optionally the undergarment is provided with tape adjusting means at the sides, over the legs and hips, and preferably the tape adjusting means include a reversible attachment means such as a "Velcro®" hook and loop fastener, lace-up ties, criss-cross laces through ties, and buckles and belts, in order that any one size may fit a wider range of people or in order that the garment can be put on a person in an opened-out configuration and not pulled up over the legs.

Optionally the garment is supplied ready for use or re-use with the adjusting means opened, so that the garment can be fitted to immobilised persons.

In a further broad aspect, the invention provides an absorbent and re-usable garment or undergarment in which an absorbent pouch capable of absorbing liquids or semi-solids discharged from a person's body is positioned, by means of panels of textile and elastic bands, adjacent a source of said discharges; said pouch having an inner stretchable lining comprised of a textile capable of admitting said liquids or semi-solids into an inner absorbent layer, wherein an outer waterproofed surface comprised of a textile is exposed and is visually indistinguishable from a surface of a conventional garment.

PREFERRED EMBODIMENT

The description of the invention to be provided herein is given purely by way of example and is not to be taken in any way as limiting the scope or extent of the invention. Throughout this specification unless the text requires otherwise, the word "comprise" and variations such as "comprising" or "comprises" will be understood to imply the inclusion of a stated integer or step or group of integers or steps but not the exclusion of any other integer or step or group of integers or steps. Each document, reference, patent application or patent cited in this text is expressly incorporated herein in their entirety by reference. Reference to cited material or information in the text should not be understood as a concession that the material or information was part of the common general knowledge or was known in New Zealand or in any other country.

DRAWINGS

FIG. 1: is a diagram of a cross-section through a pouch of a generalised undergarment, according to the invention. This is an "exploded view" for clarity from a section A-A in FIG. 2a(m).

FIG. 2a(m): is a diagram showing the appearance of Style 4 and Style 5 undergarments; the male version. FIG. 2a(f) shows the female version, at left.

FIG. 2b is derived from a photograph of a model wearing a Style 7 undergarment, showing the close fit over the body.

FIG. 3: is a diagram showing textile cutting shapes for a Style 1 undergarment FIG. 4: is a diagram showing one version of Style 1 undergarment.

FIGS. 5a and 5b shows the front and back of a style 2 undergarment.

INTRODUCTION

The concept of the invention is that it is a pouch; a launderable and re-usable discharge-collecting enclosed pouch, enclosed at an against-skin side by a hydrophilic conformable textile and enclosed on an exterior side by a hydrophobic yet gas-permeable conformable textile. The pouch contains absorbent fibrous material. The pouch is held in place by an arrangement of elastic bands, cords and/or textiles that in all respects resemble the look and feel of regular undergarments provided in the usual styles, materials, colors and sizes. That is, the "pouch retaining means" is visually similar to regular underwear. The essence of the invention is brought out by consideration of the "G-string Style". See FIGS. 11a with 11b in conjunction with the description of style 1 below.

Figures 11A, 11B:
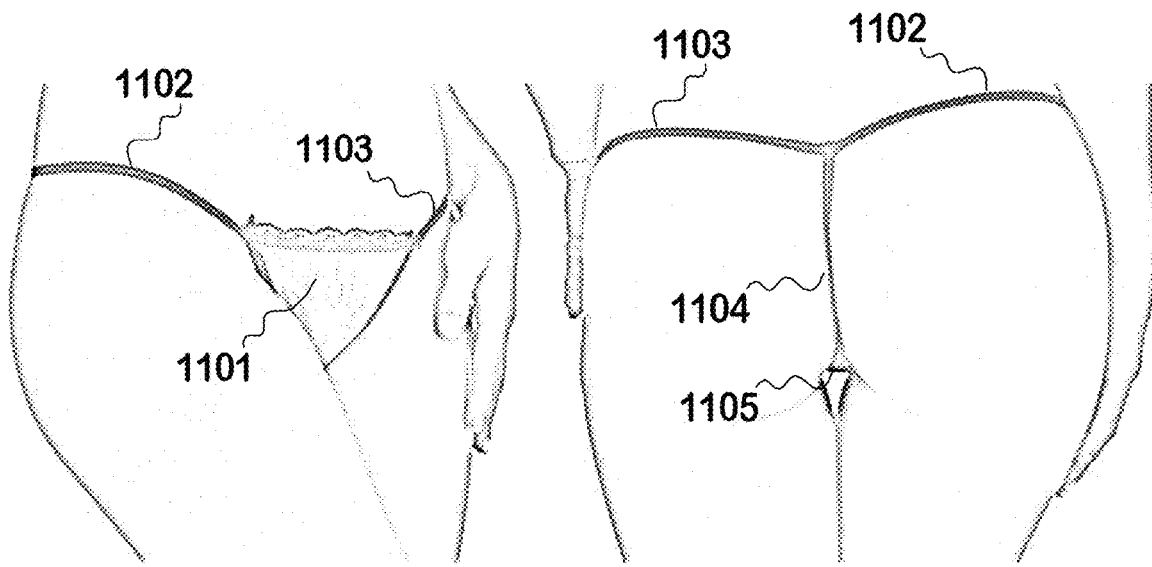
FIG. 11a is a diagram showing an oblique aspect of a Style 8 undergarment, on a model.
FIG. 11b is a diagram showing a back view of a Style 8 undergarment, on a model.

The architecture of the garment is partly determined by the intended capacity. All Styles provide a multi-layer pouch including a "quick-dry" inner layer, which transfers liquids easily and preferably at least at the rate at which they may be released from the body into an appropriate amount of an intermediate absorbtive assembly of one or more layers, which may include an active layer. The "quick-dry" aspect of the layer in contact with the skin avoids skin irritation and discomfort. The pouch, at least, has an outermost waterproofed woven textile layer. Stitching is used during assembly. The pouch is provided as part of a complete wearable undergarment and the pouch is held in position by the remainder of the garment—such as the elastic waist band and the trunk/leg panels in particular; minimally as shown in FIGS. 11a and 11b. The absorbent material is not intended to be removable and replaceable, unlike some of the prior art.

The invention will be described with reference to an example range of undergarments, as underpants, shorts, briefs or panties. Each member of the range is herein called a Style. The lower-capacity Styles do not include all of the novel aspects of the higher-capacity Styles. All Styles as described have aspects in common—to provide a re-usable "garment-mounted" discharge-absorbing construction (herein called a "pouch") constructed to lie along a midline in the garment according to location of discharge orifices, generally adjacent the urethra and perhaps also vagina and anus according to gender and requirement. Preferably the garments use stretchable, conforming fabrics and flexible pads that assist in transfer of discharge into the interior of the pouch. Any one Style is identified first by a nominal liquid capacity over a reasonable wearing time, and whether it is shaped for male or female. Any one Style may be made in a range of body sizes for example from "child" or XS small to "very large adult" or 6XL. Optionally the undergarment is provided with tape adjusting means at the sides, over the legs and hips, and preferably the tape adjusting means include a reversible attachment means such as a "Velcro®" hook and loop fastener which makes changing the undergarment for a patient in bed easier, and allows any one size to fit a wider range of people.

Preferably all of the materials selected for use in this kind of garment, especially those in contact with wet or moist skin, have a low or suppressed allergenic activity. More preferably they have no allergenic activity all; since older persons tend to be more susceptible to irritation and allergic responses. All Styles are capable of repeated laundering under hot conditions (see below) so that there is no need for early disposal.

FIG. 1 is a composite schematic diagram of a pouch containing a washable absorbent material drawn with the inner (against-body) aspect below. It is a cross-section along lines A-A in the right side (male) drawing; FIG. 2a(m). It includes the paired pouch panel components that are provided for creating a space for male-type genitalia although the diagram itself is not drawn to show a space. In FIG. 1, the waterproofed outward-facing panel 101 is shown as 101a and 101b and comprises a stretchable layer of a woven and waterproofed textile, as described below, comprising a sealing outer layer of the pouch.

A single waterproofed panel is normally used in female garments. Some Styles have a single waterproof layer 101a and 101b, while the higher capacity Styles may have two. Note that a waterproofed panel may cover the entire garment for the higher-capacity Styles. A preferred waterproofing treatment is described below.

The trunk/leg panels 102, shown as panels 102c and 102d and shown in FIG. 1 as dashed lines comprise the major part of the undergarment (although in Style 1 lace is an option). The layer between the absorbent pad of the pouch and the skin is shown as 103a and 103b (which may be combined in some Styles) and are comprised of a wettable and water-permeable "quick dry" fabric, which is preferably stretchable in order to conform to the shape of the body, and is breathable. One preferred fabric contains about 94% polyester and 6% elastane "Spandex®"; the elastane providing the elastic and shape-fitting properties. Another preferred version comprises a stretchable, knitted bamboo textile. A third version is a knitted cotton, again preferably including elastane. The cotton cloth is preferably supple and is not tightly woven. The panels do not stick to the skin even when wet. In FIGS. 1, 103a and 103b are the paired shapes used to form the inner aspect of the male pouch, while for the female pouch a single shape is used. 102c and 102d are the trunk/leg panels that extend around the person's hips to terminate against a rear portion of the pouch. The preferred stretchable nature of both the waterproofed 101a, 101b and non-waterproofed 103a, 103b panels in an undergarment that has been selected in relation to the person's body size tend to cause the layer panel 102 to be lie against the skin. t Three reasons for this are appearance, comfort, and optimised transport of discharge and moisture. The intimate contact helps liquid transfer away from the skin by capillary action into the pouch interior through the inner layer 103a, 103b. The trunk/side panels 102c, d are a lining around the person's body, joined by stitching to the edges of the pouch. The two highest-capacity example Styles 6 and 7 of the undergarment modify the non-waterproofed parts 102c, 102d by adding a covering of the waterproofed yet vapour-permeable material to the trunk/leg panels.

Note that according to this invention the waterproofed layer, which may extend to include the trunk/leg panels, is breathable to aid comfort and to reduce possible complications such as incontinence-associated dermatitis promoted by unduly wet skin. It has been found that some of the liquid caught in the absorbent pad will evaporate into the environment during a day of the undergarment being worn, so that the pad can hold more liquid over a period of use than if filled at one micturition.

When in use, incontinent-type discharges will be directed toward and are attracted by capillary action through wettable panels 103a and 103b toward the wettable absorbent volume, here shown as one layer but in two parts, allowing for the male configuration as 106a and 106b. Water movement is promoted by warmth from the wearer's body which causes moisture to evaporate from 103a and 103b and condense further out in the garment. As a result the skin-contact portions of the garment do not feel cold and clammy during use, although the garment will of course become heavier during use as liquids accumulate.

FIG. 1 also shows the stitching in diagrammatic form. 108 shows one way to secure three pieces: 103a, 102c and 101a together, preferably using flatlock or overlock stitching with multi-thread sewing; repeated on the other side. 110 and 111 indicate occasional loop stitches used to maintain the position of the absorbent layer or layers 106a, 106b within the garment pouch. Stitching 109 secures the median line of the pouch through the waterproofed panel segments 101a, 101b. The seam is provided during manufacture with a closely applied underlying non-wettable sealing tape 107 or other covering, in order to prevent leakage out of the absorbent layers 106a, 106b through the stitching itself by capillary flow and into the person's outer clothing, bypassing the waterproofed surroundings. A preferred tape application method is described below. The female version (see left side of FIG. 2a) does not include a medial stitch line joining paired parts.

The absorbent panel or assembly is preferably an absorbent woven textile such as a tufted cotton having a high capacity for absorbing liquid discharges. More layers of absorbent material may be used than are shown in FIG. 1. The inventors prefer to use absorbent cotton; best suited for price, cheapness, durability, washability, low allergenic effects, and absorbtive capacity. Other fibrous or comminuted substances, as are known to those skilled in the art, that have a high capacity for absorbing liquids could be used although it should be noted that many known options cannot withstand repeated use and repeated laundering. Some gels combine irreversibly with moisture and are suitable for one-time use. Some have the adverse characteristic of swelling when water is absorbed, whereas the selected cotton shrinks a little when wet.

Active Materials.

Discharged liquid inside the pouch may interact with optionally included active materials embedded in the absorbent layer 106a, 106b or in separate layers. For instance activated carbon which tends to remove adverse odours may be included, or colloidal silver (or particulate silver sulphate or other salts) which is bactericidal and prevents odours from forming. The entire undergarment may include some colloidal silver, which is re-usable. An iodophor or an antibiotic may be included, although soluble. Active materials may be useful at least for some medical conditions as an anti-infectious agent measure, to reduce odours, or in situations such as long-distance air travel.

FIG. 2a(m) at right shows the external appearance of the Style 5 garment 201 for males and FIG. 2a(f) at left shows the external appearance of the Style 4 garment 200 for females, both 201 from the front. 203 indicates a waist band. 204 indicates the waterproofed cover of the absorbent pouch. 205 indicates the position of an elastic leg band; not used in all versions. As shown in FIG. 2b, which is derived from a photograph of Style 7 being worn by a male model—the undergarment 200a conforms to the shape of the person's body, thanks to the preferred stretchable textile used in the outer layer, both the waterproof and the non-waterproofed portions, so that it resembles ordinary underwear. A shape aesthetic is adhered to, in keeping with current fashions, since the wearer may be lacking in confidence in terms of social interaction, and all possible encouragement should be provided. The inventors believe that the garment will be adopted more easily if it is not perceived as an obvious and possibly embarrassing accessory that amounts to a public admission of being incontinent.

The outermost layer can be selected as to fashionable colours and pattern, in order to camouflage the purpose of the garment. Selected colours are provided by use of dyed textiles. Black is one preference. Colors may be selected by a hospital or rest home management in order to provide a system for color coding such as by ward. The preferred waterproofing process (see below) does not change the color of a coloured textile. All undergarments made to date are colour-fast.

Laundering.

Underwear according to the invention could be used once and thrown away, but is intended to be washable and re-usable, many times. The inventors recommend conventional machine washing at a bactericidal temperature of at least 70° C. (158° F.) of underwear according to the invention in order to comply with standard anti-infective practices. Garments according to the invention should therefore tolerate at least 50 and perhaps 200 or more hot washes without loss of performance, in order to be useful. (The targeted micro-organisms include enteric coliforms, streptococci, staphylococci, yeasts, fungi, and the like.) An initial centrifugation (spinning) or compression step to expel incontinent liquids might be used, and/or a soaking stage in an effective disinfectant might be used. The "quick dry" layer allows water to pass in either direction, so that drying is feasible. That process is aided by the water vapour-permeable property of the waterproof outer woven textile.

Dryness is most easily assessed by weight since the "quick dry" layer tends to feel dry regardless. Any garment Style has a base weight plus the weight of held water. For example, Styles 1, 2 and 3: 50 mls capacity weigh about 130 g dry and 180 g full; Styles 4 and 5: 150 mls capacity (about 170 g dry and 320 g full), or Styles 6 and 7: 500 mls (about 200 g dry and 700 g full).

Waterproofing Panels of the Invention.

The waterproofed layer (101 or 101a, b) in all Styles at least separates the interior of the pouch from the exterior of the garment, maintaining garment integrity as long as the fluids held are within the capacity of the absorbent material 106. Waterproofed panels are water-repellent and non-wettable, yet remain permeable to water vapour. In some Styles, the waterproof layer is extended to comprise substantially the entire garment and all stitching traversing the waterproofed layer is also sealed as described below.

A number of waterproofing processes are known to those skilled in the relevant arts. The presently preferred waterproofing process used for textile panels of the various Styles relies on a particular material: fluoroalkyl acrylate copolymer. A preferred material and process uses UNIDYNE TG-410C, (Daikin Industries, No. 8 Jinyu Road (West) Advanced Materials Industrial Park, Changshu, Jiangsu 215522, China) comprising an emulsion of fluoroalkyl acrylate copolymer 10-20%, with 3-5% tripropylene glycol, less than 5% emulsifiers, and water.

In this example, five litres of the TG-401C copolymer as supplied is mixed with 100 litres of water at room temperature in a vat. The vat includes a paired roller assembly wider than the bolt of textile to be treated. The textile from the bolt is drawn in between the rollers and out again with an exposure time to the emulsion of several seconds, is passed through more rollers to remove excess emulsion, and is heat-treated or dried with hot air in order to set the emulsion on to the fabric. About 5 grams per square metre of waterproofing material is added to the textile. A single pass is used at present.

The preferred treatment is presently used with woven textiles including polyesters with elastane such as those known as "four-way stretch" or as "two-way stretch". It allows stretching and recovery. It is planned to apply the same treatment to knitted textiles. The textile should be coloured, dyed or printed as needed before waterproofing, which provides a translucent or transparent result so that selected colours or patterns will remain visible in the finished product. The ability to provide the users with a garment of pleasing or aesthetic appearance is highly desirable. The resulting waterproofed textile is permeable to gases including water vapour, and is not permeable to liquids. It retains a soft handle and does not rustle; consistent with a long life as well as with aesthetic requirements. Lace, bamboo or cotton trunk-leg panels might not be waterproofed since there may be technical difficulties in applying waterproofing material to these materials.

Internally Waterproofing Stitched Loins of the Invention.

The purpose of this aspect is to prevent liquid discharges held in the pouch from emerging through stitching (or any alternative involving passing elongate fixing material through a seam) on to the exterior of the garment. Every vulnerable stitch line is sealed from possible wicking of liquids to the exterior by application along its full length of a water-repellent material; preferably a heat-sealable water-repellent silicone tape, having a coating of hot-melt adhesive on one side, along the length of the seam and on the inner side, adjacent the absorbtive layer and hence beneath the outer surface of the garment. FIG. 1 shows (spaced apart for clarity from the layers 101a, 101b) an internal adherent non-wettable layer 107, selected from the range of: a silicone-impregnated and therefore water-repellent sealing tape, a tape including polytetrafluorethane (PTFE) and therefore a water-repellent tape, a heat-sealable tape; a silicone-rich and therefore water-repellent paint, or a water-repellent silicone ink. Use of tape is known in the manufacture of tents. The range of iron-on seam sealing tapes may be suitable. Preferably, the tape is adhered along the line of the seam by a machine that combines a hot-air flow against the thermoplastic side of the tape and over the interior side of the garment applied immediately before the tape is pressed on to the stitching by force developed between two rollers, at least one of which is driven by a motor. Alternatively a silicone paint may be applied by hand, using a dispenser resembling a felt-tip applicator. This may be used to patch up taped seams. In another version, a silicone ink may be applied along desired zones over seams by a form of screen printing process. As a result of this step, the wearer can be confident that leaked fluids, at least up to the capacity of the absorbent layer, can be fully contained for some hours.

Elastic Retaining Tapes.

The men's version of the garment is provided with a 40 mm wide band of Jacquard elastic around the waist (203 in FIG. 2). The waist band is for garment retention. For liquid retention and security, leg apertures preferably include elastic tape as a seal against liquids inadvertently running down the legs, for those Styles in which the trunk leg textile is waterproofed. If the trunk leg textile is wettable there is less reason to include elastic leg bands. (In FIG. 2b, the position of the tapes is shown by perceptible constrictions 205). One of the criteria when selecting a garment size is a leg aperture size that will seal against the thighs without being too tight. Sometimes urine is discharged faster than it can be taken up by the pouch assembly and it will be briefly free within the garment. Sometimes the nominal design capacity of the garment may be exceeded over a period of time, and the inventors have noted that people tend to underestimate their own quantity of incontinence.

When matching the requirements of an incontinent person to the available range of garments, the person, or a care giver would select a garment capable of holding the expected volume of leaked liquid over a perhaps 4 to 8 hour period between changes, match the garment to the sex of the person, match the size, and select an appearance that appeals to the person. The outermost layer can be of any desired pattern or color since the waterproofing does not significantly obscure colors. Black is one preference but that color is of course non-limiting.

TABLE

Example textile weights as grams/square metre (gsm) at standard room temperature and humidity.

| Description | gsm | Drawings reference |
| --- | --- | --- |
| Stretchable knitted (bamboo fiber) | 145 | 102, 103a, 103b |
| Absorbent tufted cotton | 209 | 106, 106a, 106b |
| Woven stretchable waterproofed polyester | 114 | 101, 101a, 101b |
| Woven stretchable polyester | 132 | 102, 103a, 103b |

Example Ranges of Styles, Colors and Nominal Capacities.

This list shows that the invention resides in part in meeting market requirements for a disorder or inconvenience that as yet is subject to stereotypes and discrimination.

1. "Women's G string"—30 ml nominal capacity.
2. "Women's light slim" 50 ml nominal capacity; lace or basic; hipster, full brief or boy leg styles, in white, beige, navy or black. (wide range shown).
3. "Men's light" 50 ml nominal capacity; black or gray; fly opening optional
4. "Women's moderate" 150 ml nominal capacity variations as example 2 except that lace trunk/leg panels are not offered.
5. "Men's moderate" 150 ml nominal capacity variations as example 3
6. "Women's ultimate" 500 ml nominal capacity
7. "Men's ultimate" 500 ml nominal capacity Style 1: "Women's G String" 30 ml Nominal Capacity.

On recognising the extent of market needs, the inventors have provided a "G-string" or "thong" option which highlights the concept of the invention as comprising a three-part discharge-holding pouch to be held in place against the body by position-maintaining means that are relatively indistinguishable from a regular undergarment. This concept is shown in fully functional form when in use in FIG. 11, as 11a (oblique front view) and 11b (back view). Here, label 1101 indicates the external, hydrophobic surface of the absorbent pouch assembly itself, for which pouch the shape of the shaped panels and pad is approximately triangular. Exposure of this surface is a characteristic of this invention.

The absorbent pouch assembly includes an innermost layer comprised of a hydrophilic "Quick-dry" textile surface including elastane that, in combination with the outer waterproofed layer 1101, fully encloses the hydrophilic absorbent pad material over the inner surface and round the sides of the pad, thereby forming the absorbent pouch, are held in place by one or more anterior elastic cords or bands under comfortable yet effective tension; part 1102 passing over the wearer's right hip and 1103 over the wearer's left hip to meet or fuse at the back as for regular G-strings, where rear or posterior thong 1104, also under appropriate tension is attached to and holds the lowest part of the triangular pouch in the perineal region at 1105, as shown in FIG. 11b. Should there be any stitching that enters the interior of the absorbent pouch, it is treated in order to be waterproof.

A lace trim decoration, or print across the top of the pouch may be preferred. After all, this may be the only garment worn when in use. This version, which has but a small absorbent pouch interior volume, cannot hold much incontinent discharge (about 30-35 ml nominal capacity). The market demand emphasises the aspect that incontinence is by no means limited to the elderly according to the stereotyped view of the incontinent person. This version, which is launderable and reusable like other Styles according to this invention, could be worn under a conventional female undergarment so that the person need not buy a new wardrobe—if the duration of an incontinent problem is expected to be short.

Style 2: "Women's Light" 50 ml Nominal Capacity.

This Style is designed to provide minimal intrusion into the user's lifestyle. Although many further variations according to the invention as described herein could be manufactured, a range offered in this nominal capacity includes: lace or cloth trunk/leg panels; hipster, full brief or boy leg styles; and a current color range is white, beige, navy or black. Patterns could easily be printed on to the trunk/leg panels and on to the waterproofed outer surface of the pouch. As shown in the example FIG. 4 (front view) the trunk/leg panels of the slim-styled undergarment 400 are made of lace, or a lace-edged knitted bamboo textile (part 301—FIG. 3), or of cotton preferably in a supple textile, perhaps knitted, rather than a tightly woven cloth. Lace may be 90% polyamide and 10% elastane (Spandex). The pouch construction 402 is detailed by the outlines in FIG. 3 while following the principles of generalised FIG. 1. The pouch is located so as to at least span the area between anus and ventral to the urethral opening, and includes an innermost layer of "quick dry" textile 302 as previously described. This layer causes liquid to be rapidly taken up from one surface—the body-contact surface—and passed to the absorbent layer. Body heat causes the body-contact surface to dry out and as a result the person does not perceive extended contact with a wet garment. Skin irritation or dermatitis is thereby minimised. The pouch of this Style provides a second cut shape 303 of absorbtive cotton textile to serve as the absorbtive layer. The pouch is enclosed from the outer side by a waterproof yet breathable layer 304 comprised of an as previously described waterproofed and woven textile comprised of about 94% polyester fiber and 6% elastane fiber. This waterproofed layer retains elasticity so that the garment tends to conform to the person's body like a fashion garment and does not hang from the body.

The three layers are sewn together around the periphery of the pouch preferably using a 5-thread flatlock/cover stitch from the outer side and preferably a 4-thread overlock on the inner side, while joining the pouch assembly to the trunk/leg panels of the garment and constructing the finished garment using a lace trim and optionally a 5 mm elastic strip inside the lace trim of the waist band.

Variation in Style 2

Figure 5C:
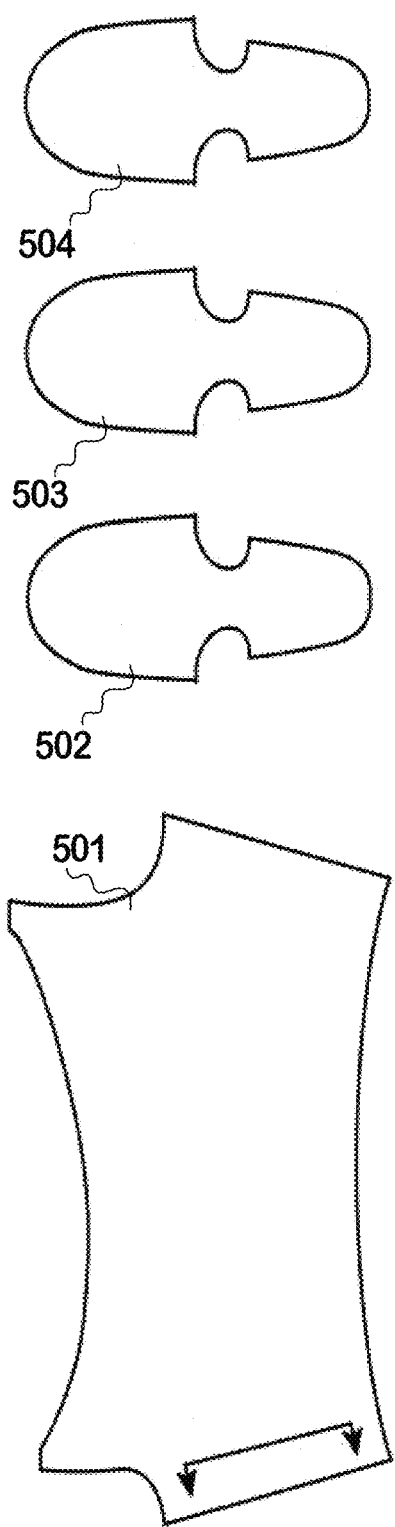
FIG. 5c is a diagram showing textile cutting shapes for a Style 2 undergarment

This variant of women's light undergarment also having a nominal capacity of 50 ml has a longer trunk, as shown in FIG. 5a (front) and FIG. 5b (back); in keeping with the style preferences of older people. FIG. 5c shows cutting templates or patterns. A garment is made from two sides 501 meeting at the pouch which is comprised of a quick dry layer 502, a cotton towelling layer 503 and an outer layer 504 in waterproof textile, as previously described. The absorbtive layer is a textile and is secured around its edges and cannot move within the pouch. The trunk/leg panels of the garment are not waterproofed. A woven polyester or a knitted bamboo textile, with stretchability, is preferred. A lace trim including a 5 mm wide elastic strip surrounds the openings.

Style 3: "Men's Light" 50 ml Nominal Capacity.

Figure 6:
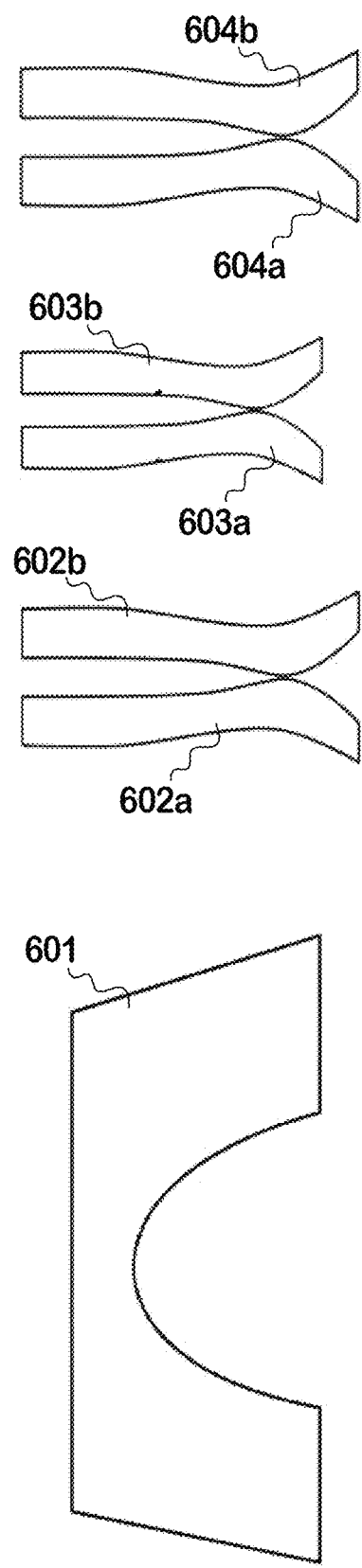
FIG. 6 is a diagram showing cutting shapes for a Style 3 undergarment

This Style introduces a shaped pouch construction adapted for persons with male genitalia, different in part because the penis is likely to leak urine from a place higher up the ventral abdomen, and partly in order to provide space for the genitals—the penis and the scrotum, for comfort. The absorbtive layer is again comprised of cotton towelling. See FIG. 6. This garment has two knitted bamboo fabric trunk/leg panels 601 that meet at front and rear at the pouch. They are not waterproofed in this Example. The diagram shows a pair of "quick dry" inner layer panels 602a and 602b of the pouch, a pair of absorbent cotton toweling forms 603a and 603b and a pair of waterproof covering forms 604a and 604b. The pouch outer layer is typically made of a woven 94% polyester, 6% elastane textile; waterproofed as previously described. Here, the required raised covering is provided by forming the pouch from sets of two-piece curved and bilaterally symmetrical shape paired panels that have curved edges, and then sewing the curved edges together. It is well known to skilled workers in many arts including undergarment manufacture that flexible sheet materials will deform and form three-dimensional shapes when curved edges are forced to come together by attachment means. As the pieces are sewn together, they bend and will provide a physical space along the lower ventral abdomen of the user for accommodating the genitals in a comfortable way. Those skilled in the art will be aware that there are other ways to deform flat textiles, particularly those comprised of thermoplastics fibers, in order to provide a permanently curved form, which may overcome having the central seam.

Style 4: "Women's Moderate" 150 ml Nominal Capacity

Figures 7, 8:
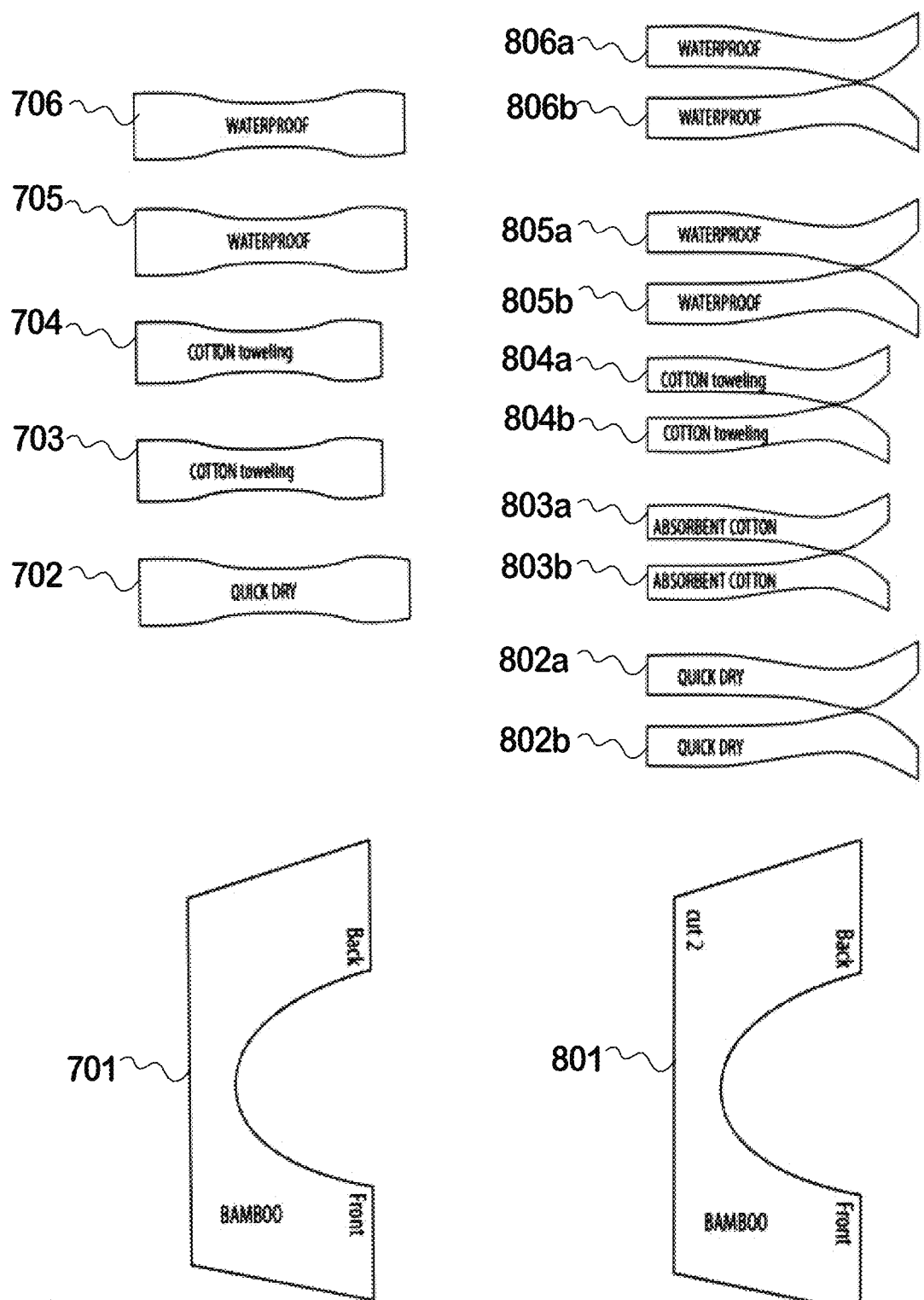
FIG. 7 is a diagram showing cutting shapes for a Style 4 undergarment
FIG. 8 is a diagram showing cutting shapes for a Style 5 undergarment
Figure 12:
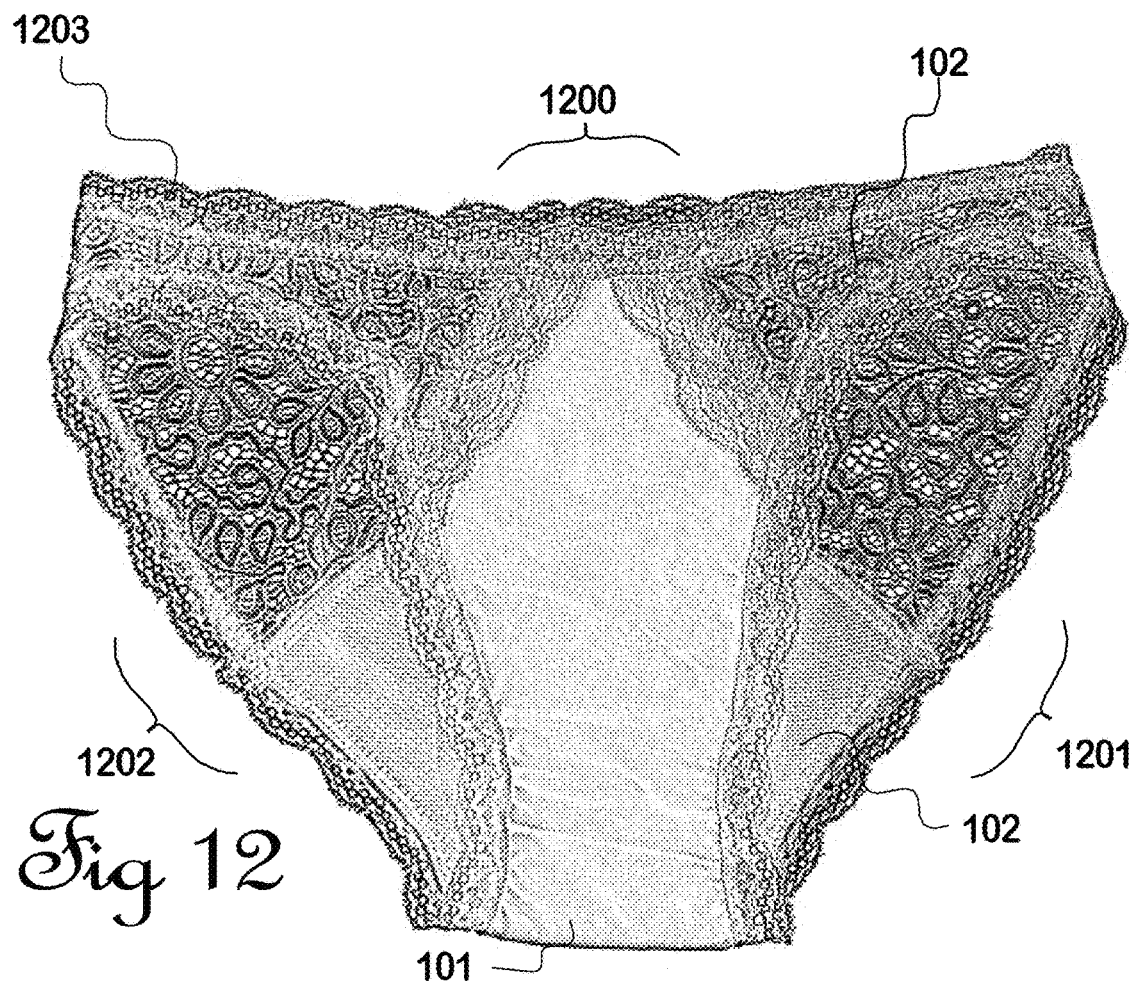
FIG. 12 shows a Style 4 "Hipster" garment with the trunk/leg panels comprised of lace.

This Style—see FIG. 7—has an absorbtive layer comprised of two or preferably three pieces or layers of cotton towelling 703 and 704, under the "quick dry" innermost layer 702. A greater volume of absorbent cotton in the pouch provides a greater capacity of about 150 ml. Two layers of waterproof material (see above for the preferred process) 705 and 706 cut to the same shape as the innermost quick-dry layer are applied over the pouch from the outer aspect. Two trunk/leg panels 701 which are not waterproofed are cut from stretchable knitted bamboo textile or a woven textile including elastane. The external frontal appearance is shown in FIG. 2a (f). FIG. 12 is a drawing adapted from a photograph showing at 1200 a production version of this Style; a Hipster cut, with lace trunk/leg panels 102, to exemplify the normal appearance of undergarments according to this invention. Using the numbering of FIG. 1, FIG. 12 shows 101 an exposed surface of an elastic, waterproofed and hence hydrophobic, yet permeable textile (caliper thickness 0.2 mm), which extends to the back of this garment and is bordered over its external perimeter by a lace border. 103 is a view of one side of the inner aspect of the absorbent pouch, which aspect is comprised of a "quick-dry" polyester/Spandex hydrophilic and elastic textile (caliper thickness 0.4 mm). The absorbtive pad (caliper thickness about 2 mm) inside the pouch is not visible. Leg openings 1201 and 1202 are visible; both bordered with elastic bands. An elastic waist band 1203 encloses an upper opening and in use will surround the person's waist.

Style 5: "Men's Moderate" 150 ml Nominal Capacity.

See FIG. 8. The outward front appearance of this style is shown in FIG. 2a (m) and in FIG. 2b. This Style has a pouch including two paired absorbent pieces which, as for Style 3, are used in a pouch (802a/b to 806a/b) that is constructed from layered, curved-edge parts. The pouch has a greater capacity of about 150 ml. The "quick-dry" innermost layer of the pouch is assembled from two parts 802a/b (103a, 103b in FIG. 1). Two layers of absorbent material; each of a left side and a right side that have been cut to the same shape as the (paired) innermost quick-dry layer are used within the pouch—shown as 803a/b and 804a/b (106a, b in FIG. 1). Cotton towelling is used. The median stitch 109 that holds the two outer waterproof layers together is covered on the inner aspect by a silicone waterproofing tape as previously described, and illustrated in FIG. 1 at 107. Use of two waterproof layers 805a/b and 806a/b over the pouch provides greater security. The waterproofing process is as previously described in this section. Two trunk/leg panels 801, reaching around the wearer's hips, preferably comprise knitted stretchable bamboo textile or a woven polyester. Noting that at least some users will be able to use a fly to urinate at some times while wearing the garment, the inventors have added a convenient fly aperture as an option for the mens' garments, comprising an opening to one side of the penis space through which the wearer can gain access to the penis for a process of controlled urination into a conventional facility. The fly opening laterally traverses a space between two portions of hydrophilic "Quick-dry" elastic cloth that tend to maintain closure of the opening.

Style 6: "Women's Ultimate" 500 ml Nominal Capacity.

Figure 9:
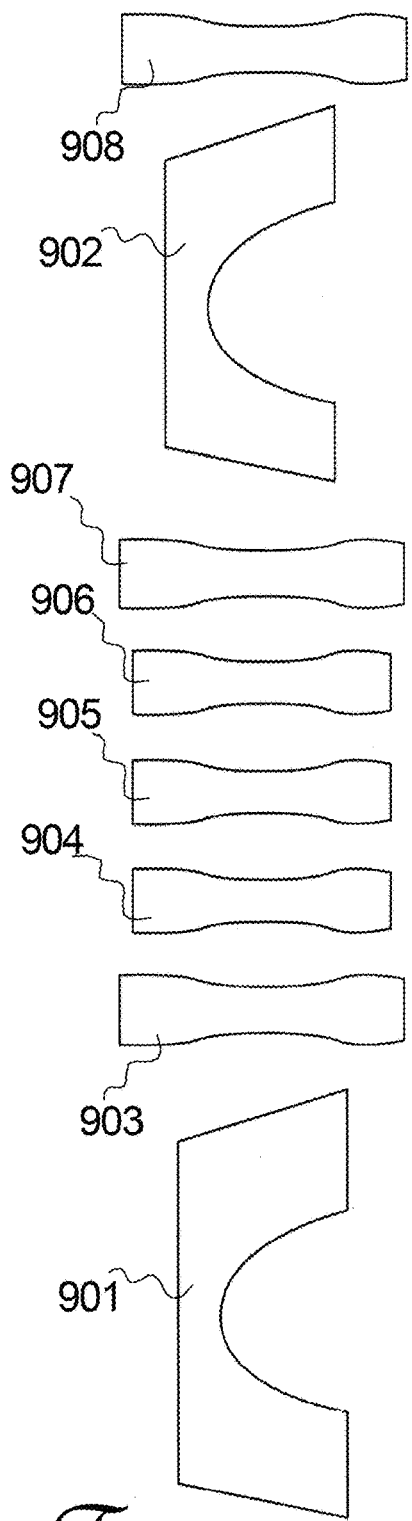
FIG. 9 is a diagram showing cutting shapes for a Style 6 undergarment

See FIG. 9. Three or four layers of absorbent cotton (904, 905, 906) within the pouch assembly provide the increased liquid capacity of this Style. The trunk/leg panels of the two-layered undergarment, covering the hips, include two pieces 902—a left side and a right side—of waterproofed yet breathable woven textile covering corresponding panels of "quick-dry" fabric. The panels pass around the wearer's body, and are stitched at each end to the edges of the pouch. The underlying layer 901 is likewise made from two pieces of the "quick dry" polyester. The elasticity of all these panels, including the trunk/leg panels, which property is retained after the preferred waterproofing process, ensures that this undergarment conforms to the shape of the person's body and holds the absorbent pouch in place. It provides an aesthetic style, not a baggy prosthetic. The trunk/leg panels adjoin the cut shape 903 of "quick dry" that forms the innermost (nearest-to-body) portion of the pouch itself. The pouch is sewn into the garment. The seams around the edge of the pouch are waterproofed also using a heat-sealable silicone tape as previously described in this section and with reference to FIG. 1 at 107 in order to provide a barrier to wicking of liquid to the exterior. The outermost layer of the pouch is two layers 907, 908 of the waterproofed textile. An elastic silicone tape around both leg holes is useful in containing excess discharge perhaps emitted at a high rate.

Style 7: "Men's Ultimate" 500 ml Capacity.

Figure 10:
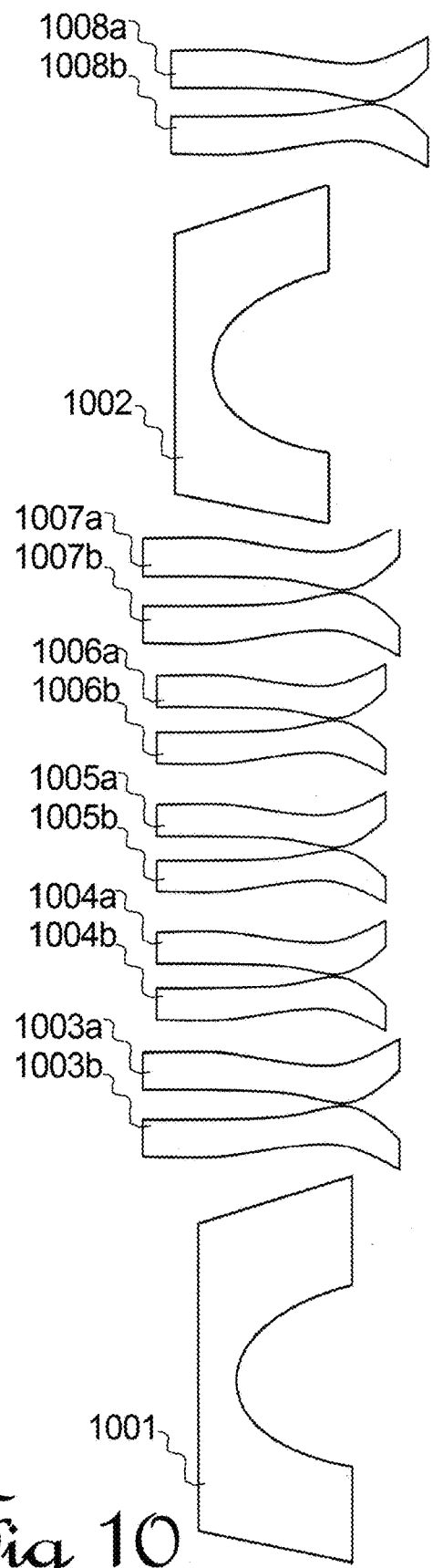
FIG. 10 is a diagram showing cutting shapes for a Style 7 undergarment

Like Style 6, this example is a two-layered undergarment wherein the stretchable trunk/leg panels are made of two pieces—a left side and a right side both shown as 1002 in FIG. 10—of waterproofed woven textile prepared as previously described in this section, overlying two pieces 1001 of the "quick dry" polyester textile, dimensioned as for the outer portion. Alternatively, one panel of a thicker microfiber cotton will serve the purpose. The trunk/leg panels pass around the person's hips, when in use, and are joined at each end to the edges of the pouch. This layer is sewn to be adjacent to (and in fluid communication with) the two sewn-together cut shapes 1003a/b of "quick dry" textile that form the innermost (nearest-to-body) portion of the pouch itself. The stretchable nature of the waterproofed material maintains adjacency. Three layers of paired shapes 1004a/b, 1005a/b, and 1006a/b of absorbent cotton are used to provide the increased liquid capacity of this Style. The pouch is finished with two sets of sewn-together cut shapes: 1007a/b, and 1008a/b of waterproofed textile as previously described in this section. All layers of this pouch are comprised of pairs of curved cut shapes in order to provide a physical space, when sewn together and in use, for the wearer's genitals. The pouch itself is sewn into the garment by stitching around its periphery using seams that are made waterproof using a heat-sealable silicone tape as previously described, and the median line of the sewn-together panels of the pouch is also waterproofed with the tape.

As an option, any version of the undergarment is provided with tape-like adjusting means at sites including the sides and over the legs and hips in order to be adjustable for specific body sizes. The tape adjusting means may be a reversible attachment means such as a "Velcro®" hook and loop fastener. If the garment is supplied with the adjusting means opened so that there are no closed holes as such for the legs in the ready-to-use configuration, the garment can be more easily fitted to immobilised persons such as patients in bed or with broken legs, without the garment having to be pulled up over the legs.

RESULTS AND ADVANTAGES

1. In a limited (35 persons) trial on prototypes of underwear according to the invention, 85% generally approved of the performance, appearance, and available variations of the invention. Some of the non-approvals originated from people whose requirements (size of garment; capacity of garment) had not been adequately matched with trial products. It was noted that 52% of the testers had experienced multiple episodes of incontinence (one reported over 20 instances) when wearing any one pair of underwear, and 60% of those testers rated the absorbtion as "very good"; the highest available rating.

2. The United States Food and Drug Administration has granted approval for underwear according to the invention in Device Class 1 to Confitex Ltd; regulation no. 876.5920 under "Garment, Protective, for Incontinence" although at the time of filing a number had not been assigned.

3. The invention provides a range of comfortable and shape-conforming, re-usable underwear having a good capacity for absorbing fluids, for use by incontinent people of any size or age and both sexes. It is noted from the literature on this topic that individual preferences must be provided for. Shape, dimensions, elasticity, color and sex adaptations are provided for within an effectively waterproof exterior. As an option, a "Velcro®" hook and loop fastener or similar tape adjusters may be provided on the outside of the legs and over hips.

4. It is an advantage to supply versions of the garment with the adjusting means opened, so that the garment can be fitted to immobilised persons without having to be pulled up over the legs.

5. Underwear according to the invention looks like regular underwear, even if seen as contours visible through overlying garments. Existing clothing can be worn over the absorbent garments. It is not bulky, in part because it employs stretchable textiles. Other people would not suspect use of incontinence undergarments. Lack of any "suspicious sounds" such as rustling lets the person wearing the undergarments go out in the community without fear of embarrassment; otherwise a significant problem. The growing number of elderly persons in the community who have varying degrees of incontinence will appreciate clothing according to the invention that is functional and in particular has a good design aesthetic 6. The waterproof property of the underwear according to the invention is included within a flexible, vapour-permeable woven textile providing for little or no risk of seal breakdown. The person's skin does not become damp and is less likely to become affected by incontinence-associated dermatitis.

7. The selected waterproofing material is capable of withstanding repeated laundering at a bactericidal temperature of over 70° C. (158° F.) in presence of hot detergent and agitation. Testers' reports are that the ease of washing and then drying was very good (38%) and good (41%).

8. Effective and reliable containment within the garments of liquids in particular, and also possible odours represent achievement of design goals. Elastic silicone leg bands in some versions prevent a transient overload of the absorbent material resulting in overflow liquids running down the wearer's legs.

9. For hospital or rest-home administrators, an "easy-care" attribute is satisfied by (a) re-use, no disassembly and reassembly after washing, and optional colour-coding to help in sorting laundered garments. Selection of passive absorbtion of fluid in the pad rather than a non-reversible gel, in combination with a vapour-permeable exterior, extends the per-use capacity over a period of for example 12 hours since some evaporation of fluid can occur. Underwear according to the invention is capable of perhaps hundreds of washes, substantially reducing the overall cost of care of an incontinent person. Expenditure on incontinence garments is reduced. The invention can be dropped into a washing machine, washed in hot water, spun and dried. Drying can be assessed by weight.

We claim:

1. An absorbent garment comprising:
   an undergarment comprising one or more of elastic cords, elastic waist bands, and elastic fabric panels including trunk/leg panels; and
   an absorbent pouch assembly inseparably attached to the undergarment operating as a pouch retainer to support the absorbent pouch assembly in connection with a human body when in use, the absorbent pouch assembly comprising
      an interior,
      an inner aspect configured to be positioned close to or in contact with a discharge area of the human body, the inner aspect comprising at least one shaped panel comprised of a wicking, hydrophilic, and permeable knitted or woven textile that includes elastic fibers,
      a flexible absorbent pad having a base, the absorbent pad being in contact with the inner aspect, the absorbent pad having a wicking, hydrophilic, and permeable fluid-absorbent composition,
      an external aspect disposed opposite the inner aspect with respect to the human body when in use, and
      at least one outer-shaped panel sealing the interior of the absorbent pouch assembly at the external aspect, the at least one outer-shaped panel being a stretchable, woven and conformable textile including elastic fibers and permeated by a fluoracrylate copolymer composition to produce a waterproof, gas-permeable permeated textile,
   wherein the garment has a nominal capacity for holding an amount of released fluid of between 30 ml and 500 ml.

2. The garment as claimed in claim 1, wherein, when the retainer includes the elastic fabric panels including the trunk/leg panels, the trunk/leg panels being shaped and comprised of woven stretchable textile, and
   wherein the trunk/leg panels are waterproofed.

3. The garment as claimed in claim 1, wherein the garment is a G-string style, and
   the absorbent pouch assembly including the permeated textile forming the at least one outer-shaped panel is held in place by a waist cord from each anterior side and a posteriorly directed cord or thong, wherein textile panels beyond the absorbent pouch assembly are absent.

4. The garment as claimed in claim 1, wherein said nominal capacity is in excess of 50 ml.

5. The garment as claimed in claim 1, further comprising adjusting devices at the sides, and over the legs and hips, in order that any one size fits a range of people.

6. An absorbent garment comprising:
   an undergarment comprising one or more of elastic cords, elastic waist bands, and elastic fabric panels including trunk/leg panels; and
   an absorbent pouch assembly inseparably attached to the undergarment operating as a pouch retainer to support the absorbent pouch assembly in connection with a human body when in use, the absorbent pouch assembly comprising
      an interior,
      an inner aspect, configured to be positioned close to or in contact with a discharge area of the human body, the inner aspect comprising at least one shaped panel comprised of a wicking, hydrophilic, and permeable knitted or woven textile that includes elastic fibers,
      a flexible absorbent pad having a base, the absorbent pad being in contact with the inner aspect, the absorbent pad having a wicking, hydrophilic, and permeable fluid-absorbent composition,
      an external aspect disposed opposite the inner aspect with respect to the human body when in use, and
      at least one outer-shaped panel sealing the interior of the absorbent pouch assembly at the external aspect, the at least one outer-shaped panel being a stretchable, knitted and conformable textile including elastic fibers and permeated by a fluoracrylate copolymer composition to produce a waterproof, gas-permeable textile.

7. The garment as claimed in claim 6, wherein the garment is produced in a range of styles each having a nominal capacity for holding an amount of released fluid of between 30 ml and 500 ml.

8. The garment as claimed in claim 7, wherein said nominal capacity is in excess of 50 ml.

* * * * *